United States Patent
Jensen et al.

(10) Patent No.: US 6,974,431 B2
(45) Date of Patent: Dec. 13, 2005

(54) APPARATUS AND METHOD FOR APPLYING A TOTAL CONTACT CAST

(75) Inventors: Jeffrey L. Jensen, Evergreen, CO (US); Brian D. Gillin, Parker, CO (US)

(73) Assignee: Medefficiency, Inc., Westminster, CO (US)

( * ) Notice: Subject to any disclaimer, the term of this patent is extended or adjusted under 35 U.S.C. 154(b) by 140 days.

(21) Appl. No.: 10/422,621

(22) Filed: Apr. 24, 2003

(65) Prior Publication Data

US 2004/0215120 A1 Oct. 28, 2004

(51) Int. Cl.[7] .................................................. A61F 5/00
(52) U.S. Cl. ............................ 602/8; 602/23; 602/27; 602/900; 128/882
(58) Field of Search .......................... 602/8, 5, 75, 23, 602/27, 20, 60, 43, 62, 63, 65, 66, 900, 903; 128/882, 892, 898; 5/648, 650, 651, 649; 601/27, 33, 34

(56) References Cited

U.S. PATENT DOCUMENTS

| | | | | |
|---|---|---|---|---|
| 2,582,242 A | * | 1/1952 | Eberl | 602/8 |
| 3,307,537 A | * | 3/1967 | Simon et al. | 602/8 |
| 3,415,243 A | * | 12/1968 | Sheldon | 602/8 |
| 3,900,024 A | * | 8/1975 | Lauber et al. | 602/8 |
| 4,235,228 A | * | 11/1980 | Gaylord et al. | 602/8 |
| 4,372,300 A | * | 2/1983 | Drennan et al. | 602/8 |
| 4,817,590 A | * | 4/1989 | Stancik, Jr. | 602/8 |
| 5,415,622 A | * | 5/1995 | Kelley | 602/5 |
| 5,891,067 A | * | 4/1999 | Reed | 602/8 |
| 6,228,044 B1 | * | 5/2001 | Jensen et al. | 602/27 |
| 6,585,671 B2 | * | 7/2003 | Rhee | 602/5 |
| 6,682,497 B2 | * | 1/2004 | Jensen et al. | 602/27 |

* cited by examiner

Primary Examiner—Fadi H. Dahbour
(74) Attorney, Agent, or Firm—Faegre & Benson LLP

(57) ABSTRACT

An improved apparatus and method for applying a total contact cast to a patient utilizes a kit of pre-packaged materials containing all of the items necessary. A uniquely designed padding strip pads the bony prominence on either side of the ankle, the top metatarsal area, and the crest of the shinbone in one unitary piece. Special cuts in the padding strip allow it to conform tightly to the bend between the foot and lower leg. The special cuts also allow the connected circular or elliptical flaps to also conform easily to the bony prominence of the ankle. Positioning the padding strip is simpler, easier, faster, and provides greater structural integrity to the overall cast. The unitary design helps prevent the padding strip from shifting when the cast is complete. An enlarged base portion of the walking heel eliminates the need for a separate wood platform for support.

26 Claims, 4 Drawing Sheets

APPARATUS AND METHOD FOR APPLYING A TOTAL CONTACT CAST

FIELD OF THE INVENTION

This invention relates to healing diabetic foot ulcerations, and more particularly, to an improved apparatus and method for applying a total contact cast to a patient so the patient can ambulate and heal at the same time.

BACKGROUND OF THE INVENTION

While diabetic foot ulcers account for the majority of neuropathic ulcers on the foot, ulcers can be also be caused by the blockage of the arteries supplying blood to the foot, malignancies, venous insufficiency, rheumatoid arthritis, and other medical conditions. The use of the Total Contact Cast should be limited to neuropathic wounds and Charcot Neuroarthropathy. Charcot Neuroarthropathy can occur from any medical condition rendering the foot insensate.

There have been many versions of "total contact casts" and this approach has proven to be efficacious. The total contact cast fits the patient leg and foot very closely. It touches or is in contact with the whole foot. The total contact cast has a layered plaster/fiberglass shell with a walking heel on the bottom. However, where the cast fits under the wound, there is a layer of soft foam that functions as the primary dressing over the wound to absorb exudates without creating maceration of the surrounding healthy tissue. The soft foam over the wound protects it while it heals and minimizes disruption of healing when it is removed at each cast change. The total contact cast off-weights the wound site or fractured bones, allowing healing to proceed without excess pressure on the area. Wearing the cast will allow most foot ulcers to typically heal in six to eight weeks. The initial cast is usually changed one to two days after it is applied. After that, a new cast is typically put on every week until the patient is ready to again wear shoes.

DETAILED DESCRIPTION OF THE INVENTION

Figure 1:
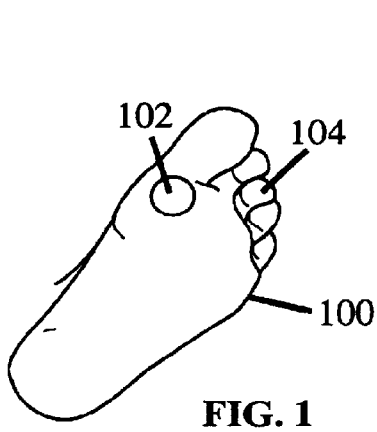
FIG. 1 shows the foot of a patient with a foot wound.

Referring now to the Figures, in which like reference numerals refer to like components thereof, FIG. 1 shows the foot of a patient with a foot wound. Referring now to FIG. 1, Foot 100 of a patient has Wound 102. Wound 102 may be located anywhere on Foot 100, and the location shown in FIG. 1 is meant to be exemplary only. Patients who have diabetes or any other underlying condition creating peripheral neuropathy can develop a Wound 102, such as a foot ulcer. The ulceration goes from the surface of the skin down into the deeper tissues. Ulcerations like this are caused by the pressure exerted from ground reactive and shearing (friction) forces that are placed on bony prominences of the foot as the patient walks. Many patients with diabetes or other related conditions do not feel the injury when it starts because of nerve damage (neuropathy). Thus, the ulceration can progress quickly in severity before it is noticed by the patient.

One method of treating Wound 102 involves placing Foot 100 in a cast with the goal of protecting the skin and relieving pressure on Wound 102. The apparatus and method of the present invention is an improved total contact cast that therapeutically helps to heal such foot sores. The total contact cast system is indicated for the treatment of Charcot Neuroarthropathy, non-infected neuropathic foot ulcers without involvement of deeper structures (tendon, joint capsule or exposed bone), pre-ulcerative conditions, and post-operative care (i.e.: Charcot reconstruction, delayed primary closures). The total contact cast should not be used on patients with ulcers that have signs of clinical infection, patients with neuropathic foot ulcers with involvement or exposure of deeper structures (tendon, joint capsule or bone), patients with ulcers that are deeper than they are in width, patients with vascular status not adequate for healing, and patients with allergies to cast components.

Figure 2:
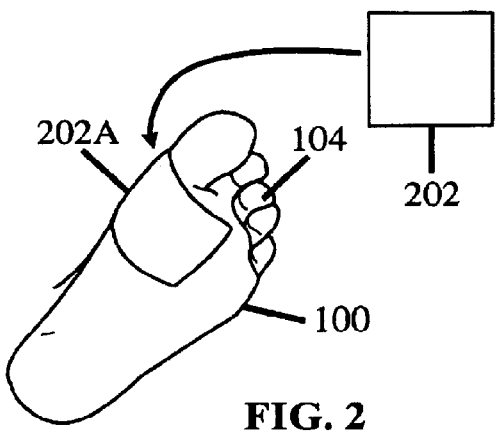
FIG. 2 shows the foot of FIG. 1 with a wound patch, or foam dressing, secured over the foot wound.

FIG. 2 shows the foot of FIG. 1 with a wound patch, or foam dressing, secured over the foot wound. Referring now to FIG. 2, before applying the total contact cast, Wound 102 is debrided and cleaned. A Wound Patch 202 (shown in top view) is typically a thin 4"×4" or 4"×5" sterile non-adhesive foam dressing, such as Optifoam™, SOF-FOAM, 3M Foam, or a sterile gauze dressing, or the like. Wound Patch 202 may be cut with scissors to better fit over Wound 102 of Foot 100. Wound Patch 202 is put over Wound 102 of Foot 100, and is shown applied as Wound Patch 202A. Typically 1" non-reactive tape (not shown) is used to secure Wound Patch 202A to Foot 100. Padding, such as lamb's wool, may be placed between Toes 104 to prevent maceration (not shown).

Figure 3:
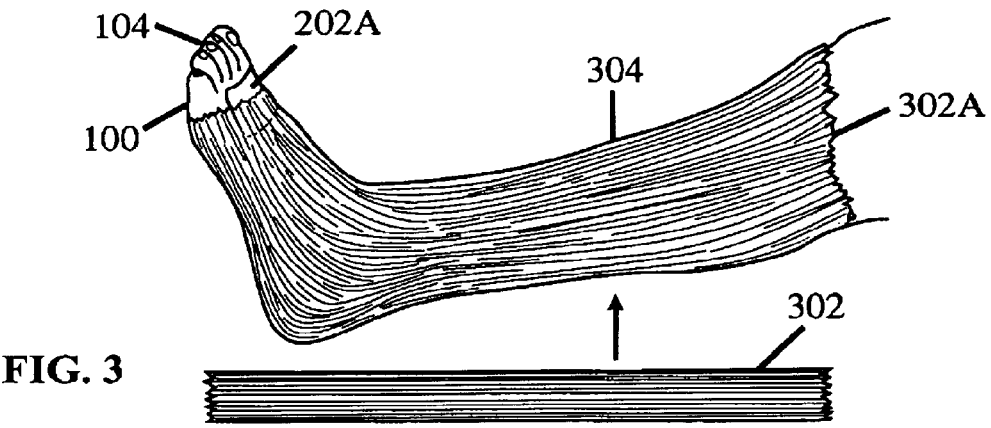
FIG. 3 shows the foot of FIG. 2 with a thin cotton stockinette positioned over the foot and lower leg.

FIG. 3 shows the foot of FIG. 2 with a thin cotton stockinette positioned over the foot and lower leg. Referring now to FIG. 3, Sock 302 (shown in top view), is typically a thin cotton stockinette, which is slipped over Foot 100 and onto Lower Leg 304, and is shown applied as Sock 302A. Sock 302/302A may be an open-toe style as shown or closed-toe (not shown). Any excess should be folded over the dorsum of the foot, trimmed, and secured with tape (not shown). Sock 302A may be positioned on Lower Leg 304 prior to applying Wound Patch 202, in which case, Sock 302A is folded back toward the ankle while Wound Patch 202 is applied, and then pulled back down to cover Toes 104.

Figure 4:
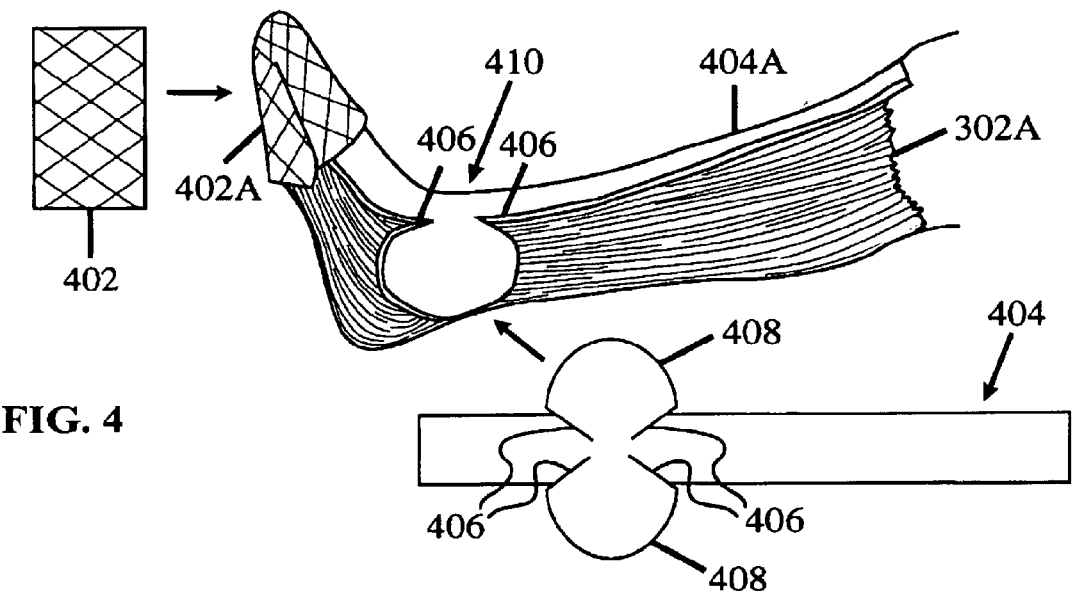
FIG. 4 shows the foot of FIG. 3 with an orthopedic felt strip secured over the top foot, ankle, and shinbone area and an adhesive backed foam secured to the toe area.

FIG. 4 shows the foot of FIG. 3 with an orthopedic felt strip secured over the top foot, ankle, and shinbone area and an adhesive backed foam secured to the toe area. Referring now to FIG. 4, Padding Strip 404 (shown in top view) is typically a felt strip or the like that is ⅛" or ¼" thick, approximately 22" long, and predominantly 3" wide throughout its length. The proximal end of Padding Strip 404 is used to pad the anterior crest of the shinbone (tibia), the distal end is used to pad the top metatarsal area, and Flaps 408 located adjacent to the distal end on opposite edges of Padding Strip 404 are used to pad the bony prominence on either side of the ankle (malleoli). Padding Strip 404 may be held in place with 1" non-reactive tape (not shown) and is shown applied as Padding Strip 404A. The unique design of Padding Strip 404 provides a strip that can pad the bony prominence on either side of the ankle, the top metatarsal area, and the anterior crest of the shinbone in one unitary piece. Diagonal Cuts 406 located where Flaps 408 join with Padding Strip 404 allow Padding Strip 404 to conform tightly to the bend at the Juncture 410 between Foot 100 and Lower Leg 304. Diagonal Cuts 406 also allow Flaps 408 to bend and conform easily to the bony prominence on either side of the ankle. Flaps 408 are typically rounded in shape, either circular or elliptical. The unique design also makes positioning Padding Strip 404/404A on Foot 100 and Lower Leg 304 much simpler, easier, and faster, and provides greater structural integrity to the overall cast. This is in contrast to using separate pieces for the strip portions covering the crest of the shinbone and the top metatarsal area, and two round pieces to cover the bony prominence on either side of the ankle as is typical for prior art total contact casts. The unitary design helps prevent Padding Strip 404A from shifting and moving when the cast is complete and the patient begins to ambulate with the cast.

To avoid cast rubs, Foam Padding 402 (shown in top view), such as ⅜" thick, 4½" by 8" Sifoam or the like, has an adhesive back. Foam Padding 402 is positioned over Toes 104, and is shown applied as Foam Padding 402A. The foam surface is striated to allow for bending ease when placed around Toes 104. Foam Padding 402A should extend far enough on top and bottom to cover the entire upper and lower surface of Toes 104, the adhesive backing sticking to Sock 302A. To help hold Foam Padding 402A in place should the adhesive backing not be sufficient, 1" non-reactive tape (not shown) may be used. Any excess portions of Foam Padding 402A should be trimmed off both medially and laterally.

Figure 5:
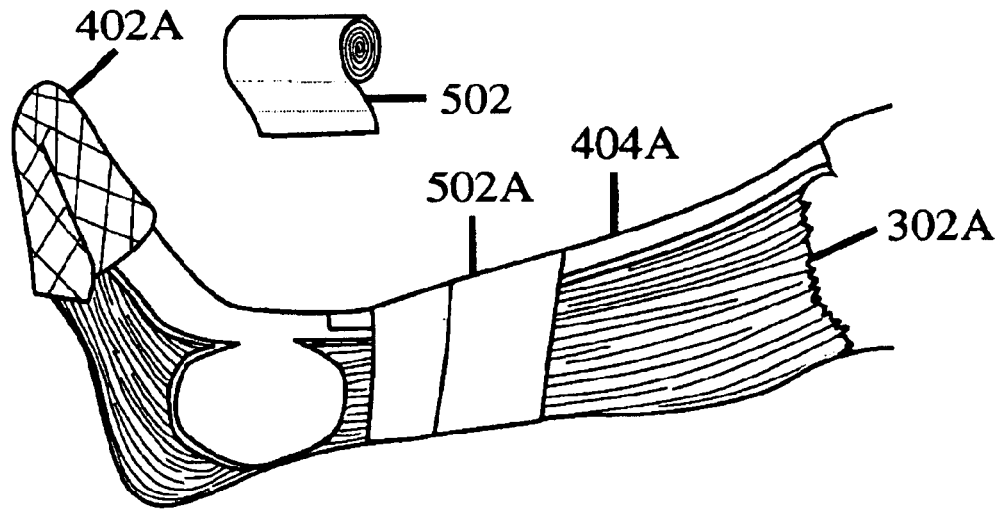
FIG. 5 shows the foot of FIG. 4 with one layer of cotton cast padding positioned just above the malleoli (ankle bones) to facilitate cast removal by minimizing the plaster/felt interface in this area.

FIG. 5 shows the foot of FIG. 4 with one layer of cotton cast padding positioned just above the malleoli (ankle bones) to facilitate cast removal by minimizing the plaster/felt interface in this area. Referring now to FIG. 5, a roll of Cast Padding 502, which is typically 4" wide Webril cast padding or the like, is wrapped circumferentially (typically a single layer) from just proximal to the medial and lateral malleoli and up about six inches toward the knee, and is shown applied as Cast Padding 502A. Cast Padding 502A is not applied so much for padding purposes, but is applied to provide assistance when the cast is removed. Cast Padding 502A allows for the easy separation of Casting Tape 602A (see FIG. 6) from Padding Strip 404A, which otherwise without Cast Padding 502A would bond tightly together, making it difficult to remove the cast.

Foot 100 and Lower Leg 304 of the patient may be placed in various positions during the various stages of applying the total contact cast as one of ordinary skill in the art will recognize. Typically, the patient is placed in a prone position with the leg flexed at the knee and the foot up in the air. The foot is maintained in a neutral position with the foot and leg being as close to ninety degrees as possible about the juncture with the ankle.

Figure 6:
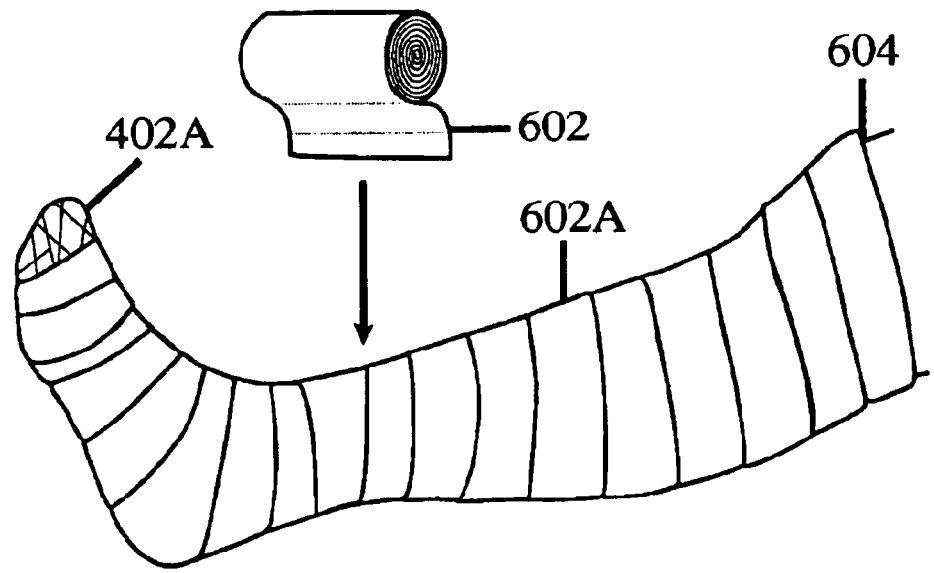
FIG. 6 shows the foot of FIG. 5 with plaster casting tape positioned over the foot and lower leg area.

FIG. 6 shows the foot of FIG. 5 with plaster casting tape positioned over the foot and lower leg area. Referring now to FIG. 6, a top portion of Sock 302A and Padding Strip 404 is folded back from the knee establishing a Trim Line 604 for the cast. A roll of Casting Tape 602, typically 4" wide, such as Johnson & Johnson Specialist® Fast Setting Plaster Bandage or Gypsona or the like, is first briefly wet and then wrapped circumferentially (typically two to three layers) covering the proximal portion of Foam Padding 402A up to Trim Line 604, and is shown applied as Casting Tape 602A. During the curing process, the casting tape is carefully molded with the fingers, especially at padded areas and the heel. Introducing dents, cracks or wrinkles in this process is avoided. It is important that this layer of casting tape conform to the exact shape of Foot 100 and Lower Leg 304 to provide a secure fit. A secure fit will prevent excessive movement of Foot 100 and Lower Leg 304 within the cast. This layer is allowed to dry before application of the next layer of casting tape.

Figure 7:
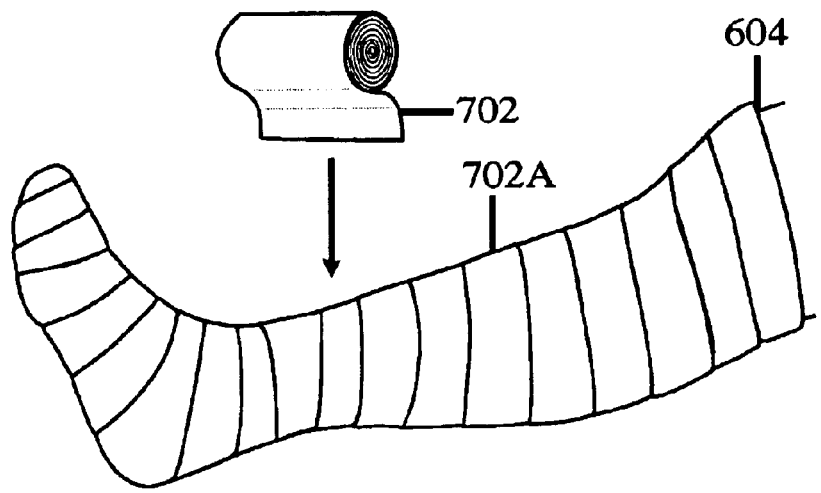
FIG. 7 shows the foot of FIG. 6 with fiberglass casting tape positioned over the foot and lower leg area.

FIG. 7 shows the foot of FIG. 6 with fiberglass casting tape positioned over the foot and lower leg area. Referring now to FIG. 7, a roll of Casting Tape 702, typically 4" wide fiberglass casting tape, such as 3M Scotchcast™ Plus Casting Tape or the like, is first briefly wet and then wrapped circumferentially (typically two to three layers) from Trim Line 604, covering Casting Tape 602A, and down over the distal portion of Foam Padding 402A, and is shown applied as Casting Tape 702A. This layer locks in the preceding layers and adds strength to the cast.

Figure 8:
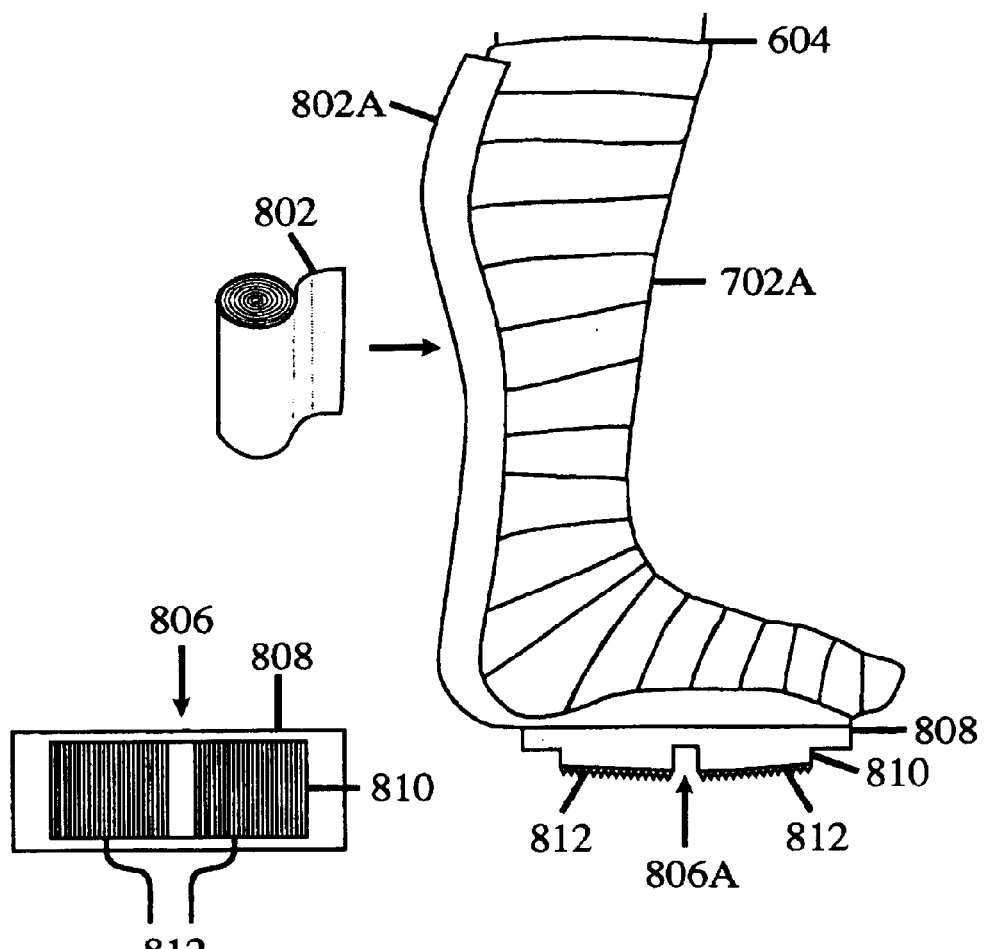
FIG. 8 shows the foot of FIG. 7 with a strip of fiberglass casting tape positioned on the back of the lower leg and bottom of the foot with a walking heel positioned on the plantar surface of the cast.

FIG. 8 shows the foot of FIG. 7 with a strip of fiberglass casting tape positioned on the back of the lower leg and bottom of the foot with a walking heel positioned on the plantar surface of the cast. Referring now to FIG. 8, a roll of Casting Tape 802, typically 3" wide fiberglass casting tape, such as 3M Scotchcast™ Plus Casting Tape or the like, is cut into a strip to form a posterior splint. Without wetting, it is applied to the back of Lower Leg 304 and the bottom of Foot 100, and is shown applied as Posterior Splint 802A. Excess material overlaps the width of bottom of Foot 100 medially, and is rolled up inwardly to fill any void in the arch area to create a flat surface for receiving a walking heel. Posterior Splint 802A may be held in place with 1" non-reactive tape (not shown).

Walking Heel 806 (shown in top view) has a Base Portion 808 and a Raised Portion 810, and is shown positioned on the plantar surface of the cast as Walking Heel 806A. Base Portion 808 serves to increase the surface area of Walking Heel 806A that contacts the plantar surface of the cast, therefore keeping Walking Heel 806A from penetrating the cast. Base Portion 808 eliminates the need for a separate wood platform to support the walking heel as is typical for prior art total contact casts. When complete, the rigidity of Base Portion 808 adds strength to the cast and gives the patient a level surface to walk on. Raised Portion 810 has Ridges 812 for providing improved traction as the patient ambulates on the cast.

Figure 9:
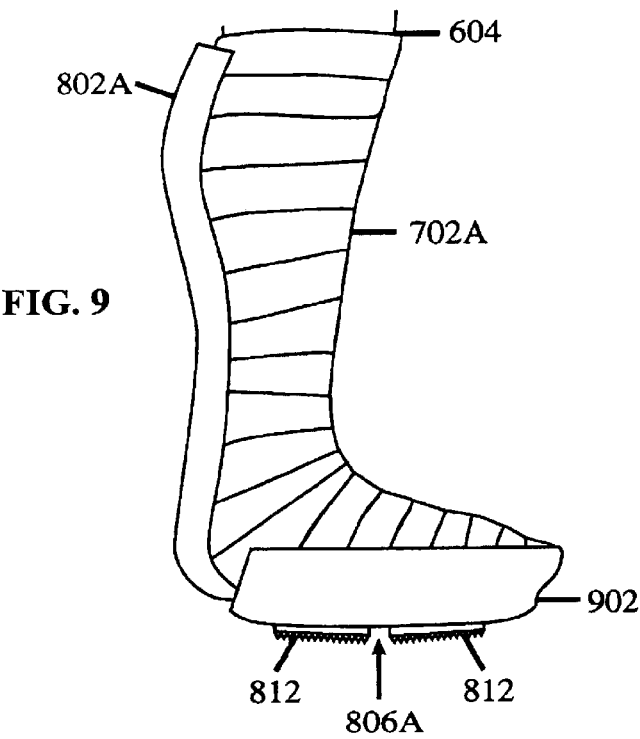
FIG. 9 shows the foot of FIG. 8 with a second fiberglass splint applied over the walking heel.

FIG. 9 shows the foot of FIG. 8 with a second fiberglass splint applied over the walking heel. Referring now to FIG. 9, a strip of Casting Tape 702 or Casting Tape 802 is used, without wetting, to form a Plantar Splint 902 which is applied over Walking Heel 806A. A cut is made in the strip to allow Walking Heel 806A to poke through, and the material is formed around Raised Portion 810 allowing Ridges 812 to be totally exposed. Plantar Splint 902 may be held in place with 1" non-reactive tape (not shown).

Figure 10:
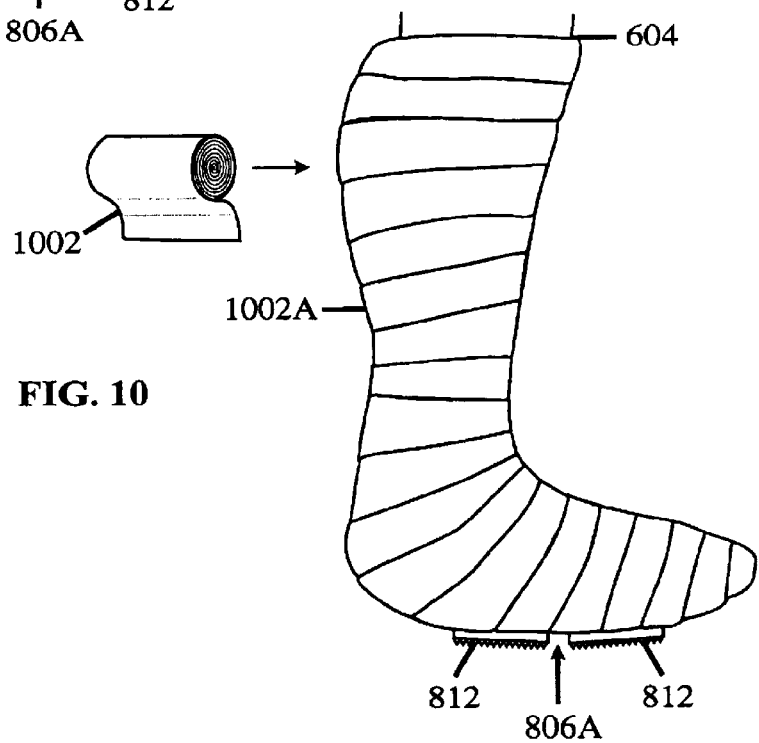
FIG. 10 shows the foot of FIG. 9 with fiberglass casting tape further securing the walking heel to the plantar surface of the cast.

FIG. 10 shows the foot of FIG. 9 with fiberglass casting tape further securing the walking heel to the plantar surface of the cast. Referring now to FIG. 10, a roll of Casting Tape 1002, typically 4" wide fiberglass casting tape, such as 3M Scotchcast™ Plus Casting Tape or the like, is first briefly wet and then wrapped circumferentially (typically two to three layers) beginning from Trim Line 604 and continuing down to Toes 104 and is shown applied as Casting Tape 1002A. Casting Tape 1002 covers over Casting Tape 702A, Posterior Splint 802A, and Plantar Splint 902. Walking Heel 806A is further secured to the plantar surface of the cast in the process, with Ridges 112 of Raised Portion 810 showing through. This final wrap provides additional strength to the cast. Weight-bearing by the patient should not be allowed for approximately fifteen minutes, or until the cast is cooled and hardened. All of the materials needed for the total contact cast can be gathered together and pre-packaged in a kit, making it extremely convenient for the health care person who applies the total contact cast of the present invention to the patient.

Because there is no posterior or lateral padding, and only anterior and toe padding in the total contact cast of the present invention, utilizing a cast saw to remove the cast without cutting, abrading, or burning the patient requires significant caution and great care. To remove the total contact cast from the patient, two parallel cuts approximately one inch apart are made, one each on either side down the anterior crest of the tibia, which is over the area covered by Padding Strip 404A. Cuts are next made medially and laterally over the malleoli, which is also over the area covered by Padding Strip 404A. Next, a cut across Toes 104 is made, medial to lateral, which is over the area covered by Foam Padding 402A. Thus, all the cuts are made over areas that are padded, preventing injury to the patient. The cast can now be opened with small spreaders, and Padding Strip 404A removed. Sock 302A can be cut from top to bottom using blunt scissors. Foot 100 and Lower Leg 304 can now be easily removed from the cast.

Having described the present invention, it will be understood by those skilled in the art that many changes in construction and widely differing embodiments and applications of the invention will suggest themselves without departing from the scope of the present invention.

What is claimed is:

1. In a method for applying a total contact cast to a patient, the method comprising applying a wound patch to a foot wound of the patient, positioning a sock over a foot and a lower leg of the patient, positioning a foam padding over a plurality of toes of the patient, positioning a cast padding over the lower leg, applying a casting tape over the foot and the lower leg, and securing a wood platform and a walking heel on the plantar surface, wherein the improvement comprises the steps of:

(a) positioning a proximal end of a padding strip over an anterior crest of a tibia over the sock on the lower leg;

(b) positioning a distal end of said padding strip over a top metatarsal area over the sock on the foot;

(c) positioning a first flap adjacent to said distal end and located on a first edge of said padding strip over a medial malleoli over the sock on the foot; and (d) positioning a second flap adjacent to said distal end and located on a second edge of said padding strip and aligned opposite with said first flap over a lateral malleoli over the sock on the foot.

2. A method according to claim 1 wherein said padding strip further comprises a plurality of diagonal cuts located where said first and second flaps join with said padding strip along said first and second edges, wherein said plurality of diagonal cuts assist in said positioning steps by allowing said first and second flaps to bend and conform to said medial and lateral malleoli, and allowing said padding strip to conform to a bend at a juncture of the foot and the lower leg of the patient.

3. A method according to claim 1 wherein the step of applying said casting tape further comprises the steps of:

applying a plaster casting tape layer over the lower leg and the foot, covering the cast padding, said padding strip, said first and second flaps, and a proximal portion of the foam padding;

applying a first fiberglass casting tape layer over the lower leg and the foot, covering said plaster casting tape layer and a distal portion of the foam padding; and applying a second fiberglass casting tape layer over the lower leg and the foot, covering said first fiberglass casting tape layer and securing the wood platform and the walking heel to the plantar surface.

4. In a method for applying a total contact cast to a patient, the method comprising applying a wound patch to a foot wound of the patient, positioning a sock over a foot and a lower leg of the patient, positioning a padding strip over an anterior crest of a tibia and a top metatarsal area of the patient, positioning a first circular pad and a second circular pad over a medial malleoli and lateral malleoli respectively of the patient, positioning a foam padding over a plurality of toes of the patient, positioning a cast padding over the lower leg, and applying a casting tape over the foot and the lower leg, wherein the improvement comprises the steps of:

(a) positioning a base portion of a walking heel on a plantar surface; and (b) securing said walking heel having said base portion with the casting tape to said plantar surface, wherein said base portion increases a surface area of said walking heel in contact with said plantar surface, preventing said walking heel from penetrating the total contact cast.

5. A method according to claim 4 wherein said securing step further comprises:

allowing a raised portion of said walking heel to show through the casting tape, said raised portion further comprising a plurality of ridges, wherein said plurality of ridges on said raised portion provides improved traction for ambulation by the patient with the total contact cast.

6. A method according to claim 4 wherein the step of applying the casting tape further comprises the steps of:

applying a plaster casting tape layer over the lower leg and the foot, covering the cast padding, the padding strip, the first and second circular pads, and a proximal portion of the foam padding;

applying a first fiberglass casting tape layer over the lower leg and the foot, covering said plaster casting tape layer and a distal portion of the foam padding; and applying a second fiberglass casting tape layer over the lower leg and the foot, covering said first fiberglass casting tape layer and securing said walking heel having said base portion to said plantar surface while allowing said raised portion of said walking heel to show through said second fiberglass casting tape layer.

7. A method according to claim 6 further comprising the steps of:

forming a posterior splint from a fiberglass casting tape;

applying said posterior splint to a posterior side of the lower leg and said plantar surface, rolling an excess of said fiberglass casting tape inwardly to fill a void in an arch area of the foot to create a flat surface for receiving said base portion of said walking heel;

forming a plantar splint from said fiberglass casting tape; making a cut in said plantar splint; and applying said plantar splint over said walking heel, allowing said raised portion of said walking heel to show through said cut.

8. In a method for applying a total contact cast to a patient, the method comprising applying a wound patch to a foot wound of the patient, positioning a sock over the foot and the lower leg of the patient, positioning a foam padding over a plurality of toes of the patient, positioning a cast padding over the lower leg, and applying a casting tape over the foot and the lower leg, wherein the improvement comprises the steps of:

(a) positioning a proximal end of a padding strip over an anterior crest of a tibia over the sock on the lower leg;

(b) positioning a distal end of said padding strip over a top metatarsal area over the sock on the foot;

(c) positioning a first flap adjacent to said distal end and located on a first edge of said padding strip over a medial malleoli over the sock on the foot;

(d) positioning a second flap adjacent to said distal end and located on a second edge of said padding strip and aligned opposite with said first flap over a lateral malleoli over the sock on the foot;

(e) positioning a base portion of a walking heel on a plantar surface; and (f) securing said walking heel having said base portion with the casting tape to said plantar surface, wherein said base portion increases a surface area of said walking heel in contact with said plantar surface, preventing said walking heel from penetrating the total contact cast.

9. A method according to claim 8 wherein said padding strip further comprises a plurality of diagonal cuts located where said first and second flaps join with said padding strip along said first and second edges, wherein said plurality of diagonal cuts assist in said positioning steps (a) through (d) by allowing said first and second flaps to bend and conform to said medial and lateral malleoli, and allowing said padding strip to conform to a bend at a juncture of the foot and the lower leg of the patient.

10. A method according to claim 8 wherein said securing step further comprises:

allowing a raised portion of said walking heel to show through the casting tape, said raised portion further comprising a plurality of ridges, wherein said plurality of ridges on said raised portion provides improved traction for ambulation by the patient with the total contact cast.

11. A method according to claim 8 wherein the step of applying the casting tape further comprises the steps of:

applying a plaster casting tape layer over the lower leg and the foot, covering the cast padding, said padding strip, said first and second flaps, and a proximal portion of the foam padding;

applying a first fiberglass casting tape layer over the lower leg and the foot, covering said plaster casting tape layer and a distal portion of the foam padding; and applying a second fiberglass casting tape layer over the lower leg and the foot, covering said first fiberglass casting tape layer and securing said walking heel having said base portion to said plantar surface while allowing said raised portion of said walking heel to show through said second fiberglass casting tape layer.

12. A method according to claim 11 further comprising the steps of:

forming a posterior splint from a fiberglass casting tape;

applying said posterior splint to a posterior side of the lower leg and said plantar surface, rolling an excess of said fiberglass casting tape inwardly to fill a void in an arch area of the foot to create a flat surface for receiving said base portion of said walking heel;

forming a plantar splint from said fiberglass casting tape;

making a cut in said plantar splint; and applying said plantar splint over said walking heel, allowing said raised portion of said walking heel to show through said cut.

13. A total contact cast having a wound patch applied to a foot wound of a patient, a sock positioned over a foot and a lower leg of the patient, a foam padding positioned over a plurality of toes of the patient, a cast padding positioned over the lower leg, and a casting tape applied over the foot and the lower leg securing a wood platform and a walking heel on the plantar surface, wherein the improvement comprises:

a padding strip having proximal and distal ends, said padding strip further comprising:
 a first flap adjacent to said distal end and located on a first edge of said padding strip; and
 a second flap adjacent to said distal end and located on a second edge of said padding strip and aligned opposite with said first flap, wherein said padding strip is positioned over the sock on the patient, said proximal end of said padding strip is positioned over an anterior crest of a tibia, said distal end of said padding strip is positioned over a top metatarsal area, and said first and second flaps are positioned over a medial malleoli and a lateral malleoli respectively.

14. The total contact cast according to claim 13 wherein said padding strip further comprises:

a plurality of diagonal cuts located where said first and second flaps join with said padding strip along said first and second edges, wherein said plurality of diagonal cuts allow said first and second flaps to bend and conform to said medial and lateral malleoli and allow said padding strip to conform to a bend at a juncture of the foot and the lower leg of the patient.

15. The total contact cast according to claim 13 wherein said first and second flaps are rounded in shape.

16. The total contact cast according to claim 13 wherein the casting tape further comprises:

a plaster casting tape applied over the lower leg and the foot, covering the cast padding, said padding strip, said first and second flaps, and a proximal portion of the foam padding;

a fiberglass casting tape, wherein a first layer of said fiberglass casting tape is applied over the lower leg and the foot, covering said plaster casting tape and a distal portion of the foam padding; and further wherein a second layer of said fiberglass casting tape is applied over the lower leg and the foot, covering said first layer of said fiberglass casting tape and securing the wood platform and the walking heel to the plantar surface.

17. A total contact cast having a wound patch applied to a foot wound of a patient, a sock positioned over a foot and a lower leg of the patient, a padding strip positioned over an anterior crest of a tibia and a top metatarsal area of the patient, a first circular pad and a second circular pad positioned over a medial and lateral malleoli respectively of the patient, a foam padding positioned over a plurality of toes of the patient, a cast padding positioned over the lower leg, and a casting tape applied over the foot and the lower leg, wherein the improvement comprises:

a walking heel having a base portion,
wherein said base portion of said walking heel is positioned on a plantar surface and secured with the casting tape, and further wherein said base portion increases a surface area of said walking heel in contact with said plantar surface, preventing said walking heel from penetrating the total contact cast.

18. The total contact cast according to claim 17 wherein said walking heel further comprises:
   a raised portion, said raised portion further comprising a plurality of ridges,
   wherein said plurality of ridges on said raised portion provides improved traction for ambulation by the patient with the total contact cast.

19. The total contact cast according to claim 17 wherein the casting tape further comprises:
   a plaster casting tape applied over the lower leg and the foot, covering the cast padding, the padding strip, the first and second circular pads, and a proximal portion of the foam padding;
   a fiberglass casting tape, wherein a first layer of said fiberglass casting tape is applied over the lower leg and the foot, covering said plaster casting tape and a distal portion of the foam padding; and
   further wherein a second layer of said fiberglass casting tape is applied over the lower leg and the foot, covering said first layer of said fiberglass casting tape and securing said walking heel having said base portion to said plantar surface.

20. The total contact cast according to claim 19 further comprising:
   a posterior splint formed from said fiberglass casting tape, wherein said posterior splint is applied to a posterior side of the lower leg and said plantar surface, and further wherein an excess of said fiberglass casting tape is rolled inwardly to fill a void in an arch area of the foot to create a flat surface for receiving said base portion of said walking heel; and
   a plantar splint formed from said fiberglass casting tape having a cut therein, wherein said plantar splint is applied over said walking heel, allowing said raised portion of said walking heel to show through said cut.

21. A total contact cast having a wound patch applied to a foot wound of a patient, a sock positioned over a foot and a lower leg of the patient, a foam padding positioned over a plurality of toes of the patient, a cast padding positioned over the lower leg, and a casting tape applied over the foot and the lower leg, wherein the improvement comprises:

a padding strip having proximal and distal ends, said padding strip further comprising:
   a first flap adjacent to said distal end and located on a first edge of said padding strip;
   a second flap adjacent to said distal end and located on a second edge of said padding strip and aligned opposite with said first flap; and a walking heel having a base portion;

wherein said padding strip is positioned over the sock on the patient, said proximal end of said padding strip is positioned over an anterior crest of a tibia, said distal end of said padding strip is positioned over a top metatarsal area, and said first and second flaps are positioned over a medial malleoli and a lateral malleoli respectively, and wherein said base portion of said walking heel is positioned on a plantar surface and secured with the casting tape, and further wherein said base portion increases a surface area of said walking heel in contact with said plantar surface, preventing said walking heel from penetrating the total contact cast.

22. The total contact cast according to claim 21 wherein said padding strip further comprises:
   a plurality of diagonal cuts located where said first and second flaps join with said padding strip along said first and second edges,
   wherein said plurality of diagonal cuts allow said first and second flaps to bend and conform to said medial and lateral malleoli and allow said padding strip to conform to a bend at a juncture of the foot and the lower leg of the patient.

23. The total contact cast according to claim 21 wherein said first and second flaps are rounded in shape.

24. The total contact cast according to claim 21 wherein said walking heel further comprises:
   a raised portion, said raised portion further comprising a plurality of ridges,
   wherein said plurality of ridges on said raised portion provides improved traction for ambulation by the patient with the total contact cast.

25. The total contact cast according to claim 21 wherein the casting tape further comprises:
   a plaster casting tape applied over the lower leg and the foot, covering the cast padding, said padding strip, said first and second flaps, and a proximal portion of the foam padding;
   a fiberglass casting tape, wherein a first layer of said fiberglass casting tape is applied over the lower leg and the foot, covering said plaster casting tape and a distal portion of the foam padding; and
   further wherein a second layer of said fiberglass casting tape is applied over the lower leg and the foot, covering said first layer of said fiberglass casting tape and securing said walking heel having said base portion to said plantar surface.

26. The total contact cast according to claim 25 further comprising:
   a posterior splint formed from said fiberglass casting tape, wherein said posterior splint is applied to a posterior side of the lower leg and said plantar surface, and further wherein an excess of said fiberglass casting tape is rolled inwardly to fill a void in an arch area of the foot to create a flat surface for receiving said base portion of said walking heel; and
   a plantar splint formed from said fiberglass casting tape having a cut therein, wherein said plantar splint is applied over said walking heel, allowing said raised portion of said walking heel to show through said cut.

* * * * *